United States Patent [19]

Roeschlaub et al.

[11] 4,213,328
[45] Jul. 22, 1980

[54] APPARATUS FOR FLUID PRESSURE TESTING OF ENGINE CYLINDER HEADS AND SIMILAR PARTS

[75] Inventors: Ronald C. Roeschlaub, Los Angeles; Albert Fegel, Whittier, both of Calif.

[73] Assignee: Irontite Products, Inc., El Monte, Calif.

[21] Appl. No.: 15,850

[22] Filed: Feb. 27, 1979

[51] Int. Cl.² .................................. G01M 15/00
[52] U.S. Cl. ........................................ 73/49.7
[58] Field of Search .................. 73/49.7, 47, 49.8; 138/89; 215/355

[56] References Cited

U.S. PATENT DOCUMENTS

| | | | |
|---|---|---|---|
| 1,481,505 | 1/1924 | Crass | 215/355 X |
| 1,856,023 | 4/1932 | Brandt | 73/47 |
| 2,465,727 | 3/1949 | Jensen | 138/89 X |
| 3,360,984 | 1/1968 | Salsbury et al. | 73/49.7 |
| 3,608,369 | 9/1971 | Wilkinson | 73/49.7 X |
| 3,751,978 | 8/1973 | Crawford | 73/49.7 |
| 3,973,429 | 8/1976 | Durgan et al. | 73/49.7 |
| 4,157,028 | 6/1979 | Moffett | 73/49.7 |

*Primary Examiner*—Donald Watkins
*Assistant Examiner*—Joseph W. Roskos
*Attorney, Agent, or Firm*—Whann & McManigal

[57] ABSTRACT

An apparatus for fluid pressure testing of engine cylinder heads and similar parts by sealing the fluid circulating jacket ports and subjecting the head to a fluid pressure comprising, a lockable pivoting frame structure on which the head is positioned and secured by clamp bars, individual port closure members secured to the cylinder head by clamps and bolts so as to seal the cylinder head ports and a modified port closure member when connected to a pressurized fluid supply conduit allows a pressurized fluid to be introduced into the fluid circulating jacket.

6 Claims, 11 Drawing Figures

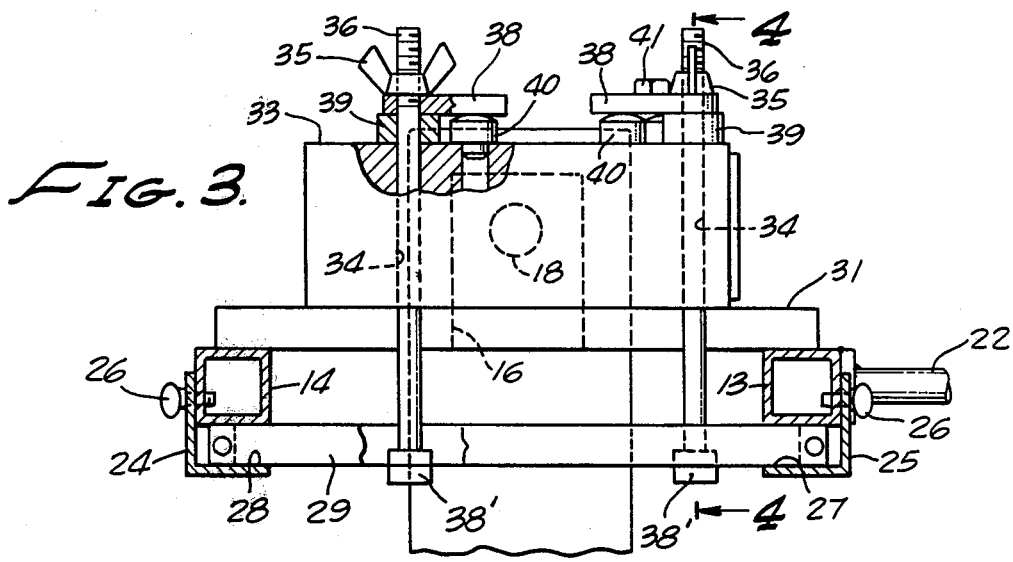
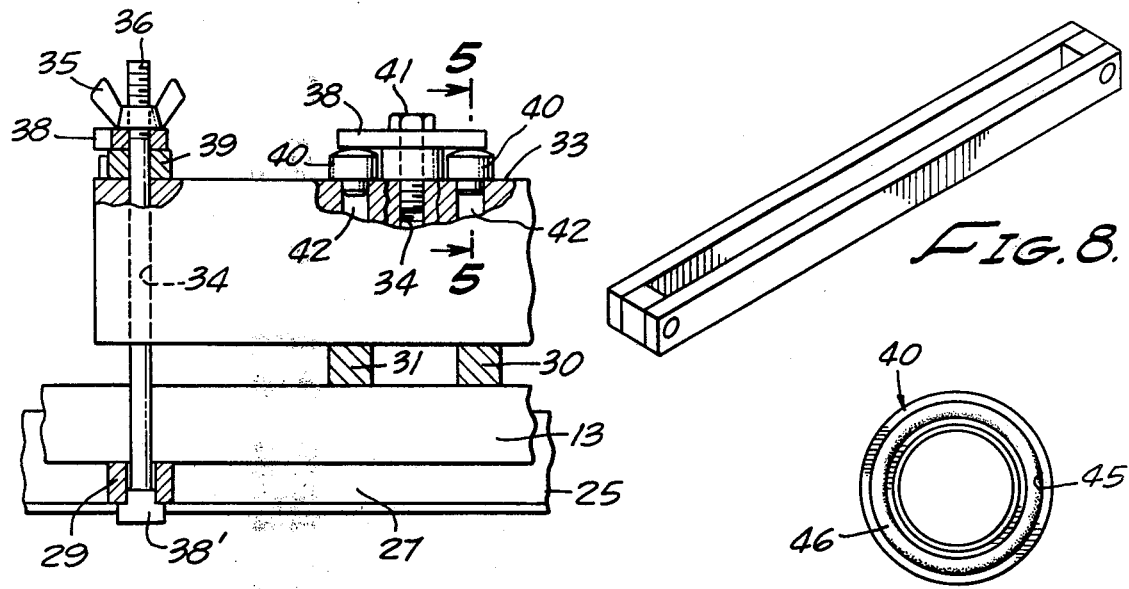
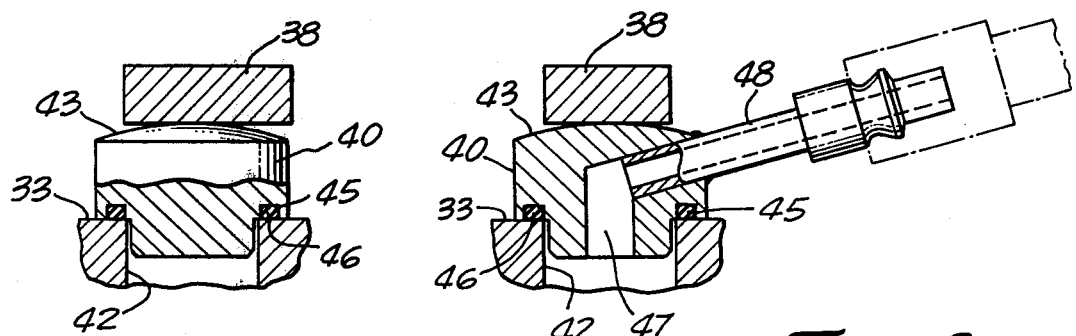

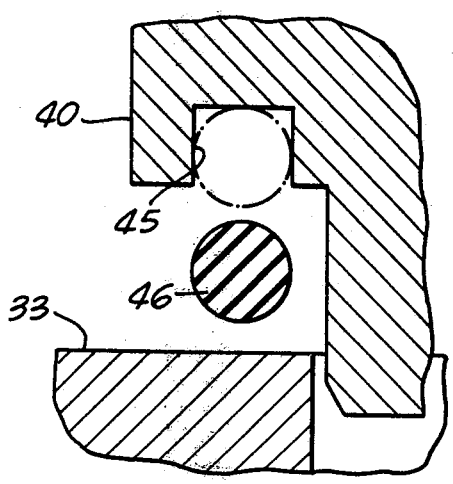
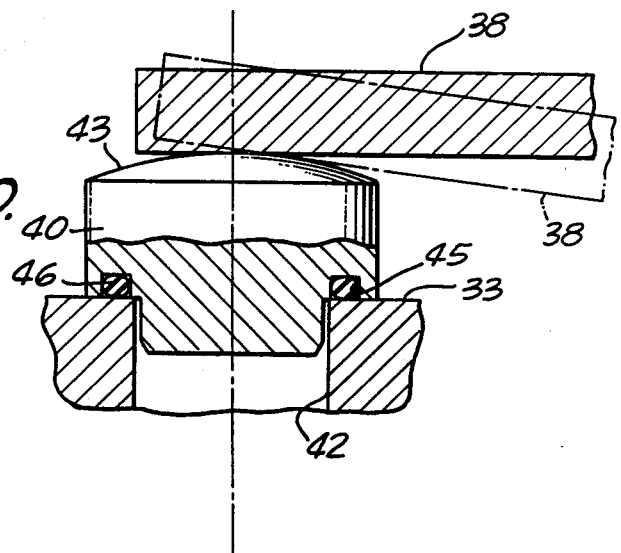
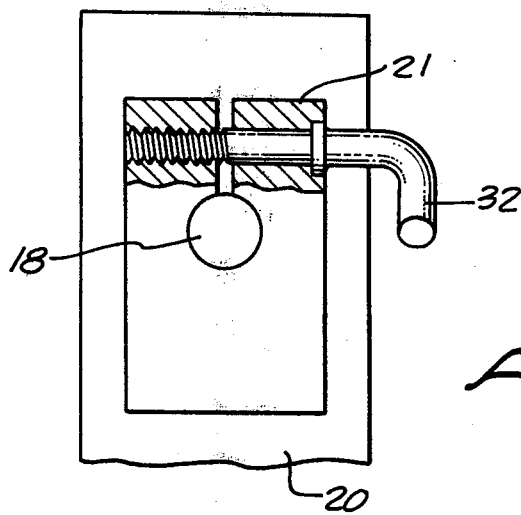

APPARATUS FOR FLUID PRESSURE TESTING OF ENGINE CYLINDER HEADS AND SIMILAR PARTS

BACKGROUND OF THE INVENTION

The present invention relates generally to the testing of engine components for leaks or cracks in fluid circulating jackets within the component and in particular to diesel engine cylinder heads, by utilizing an improved apparatus on which engine cylinder heads are mounted, prepared for testing and then tested by subjecting the head fluid-circulating jacket to a pressurized fluid whereby cracks or leaks may be detected.

Prior art teaches that engine cylinder heads and the like can be tested for leaks by sealing off the ports of the water-jacket conduits and thereby subjecting the conduits to a fluid under pressure. By utilizing a soap solution or other suitable solution it is then possible to determine the location of leaks or cracks in the defective head. The damaged portion of the head can then be repaired by conventional means.

A major problem in executing such a testing procedure in diesel engine cylinder heads and the like is manipulating the heavy cast iron heads prior to and during the test itself and sealing off and pressurizing the heads sufficiently to detect defects that are readily apparent only under actual operating pressures, yet enabling the testing and subsequent repair procedures to be conducted efficiently and rapidly.

Diesel engines by virtue of their higher compression pressures are by necessity significantly heavier than convential gasoline engines and a cylinder head from a diesel engine may weigh as much as five hundred pounds. Conventional testing and repair procedures of such components as disclosed by the prior art hold the head to be tested in a fixed position preventing its manipulation during testing and subsequent repair. The fixed position of the head inhibits a rapid and complete inspection of the head for defects and makes access to the head for repair purposes difficult.

Conventional procedures for the fluid pressure testing of engine cylinder heads often require the use of custom-made plates and gaskets to seal off the water jacket conduit ports so that a pressurized fluid may be introduced into the sealed water jacket enabling the location of cracks or leaks. Given that the variety of diesel engines on the world market is in excess of 500, for a testing facility to provide a complete testing and repair service it would be required to maintain a complete set of expensive, custom-made plates and gaskets, each for use on the cylinder head of a particular design. Furthermore, conventional apparatus utilizing custom-made plates and gaskets are constructed such that much of the cylinder head gasket mating surface is covered during the testing procedure. Thus repairs to the defective head are difficult or impossible to make without removing the port closure plate.

An attempt by the prior art to solve the preceding problem has resulted in the apparatus of Salsbury et al, U.S. Pat. No. 3,360,984, whereby cylinder heads could be more rapidly and easily set up for testing; and which would permit the making of repairs without having to disconnect or remove the testing apparatus, thus enabling its use for further testing after repairs have been made. While the Salsbury apparatus has succeeded in shortening the testing and repair times for cylinder heads it has an inherent disadvantage in its inability to allow rapid positioning and manipulation of the cylinder head on the testing apparatus as the head is in a fixed position supported by adjustable jacks or blocks and shims. Furthermore, the engine mating gasket engaging surface is positioned closely below or within a frame structure used to support water jacket port closure means. This fixed configuration of the head within a frame assembly inhibits rapid setup, testing and repair of the head on the apparatus as the head cannot be easily inspected for cracks or leaks except on the gasket engaging surface. An additional disadvantage of the Salsbury apparatus is its inability to have the surface of the gasket engaging surface relatively free of clamps, plates or other obstructions so as to allow greater access to the head surface for repair purposes.

The present invention eliminates the above shortcomings by providing an apparatus for the fluid pressure testing of engine cylinder heads and the like which is of simpler design, of more economical construction, which can be universally used with engine cylinder heads, is more readily and rapidly set up, and enable manipulation of the head while mounted in the test apparatus promoting faster inspection and repair without remounting or removing the head from the testing apparatus. In addition the invention described herein provides a simpler means for sealing water jacket ports thereby allowing higher test pressures without the elaborate and cumbersome port closure devices that obscure the head surface and make repair procedures without removal of the test equipment difficult.

SUMMARY OF THE INVENTION

With the foregoing in mind it is an object of our invention to provide a testing apparatus for engine components which is of simple and economical design, which can be used for pressurized testing of all types of engine cylinder heads, which allows the heads to be easily manipulated and positioned prior to and during the testing procedures enabling rapid and complete testing of the part without disconnecting or removing the test apparatus, thus enabling its use for further testing after necessary repairs are made.

Another object is to provide testing apparatus of the character described which includes means for rapidly positioning and securing an engine cylinder head to be fluid pressure tested on the apparatus such that the head surface is exposed and easily accessible for the repair of cracks or leaks.

Another object is to provide lockable pivoting means so to enable the cylinder head mounted on the testing apparatus to be positioned at a desired angular position facilitating testing, and repair procedures.

Still another object is to provide testing apparatus of the character described which includes unique port closure structures for sealing off the fluid jacket conduit ports while occupying a minimal area on the head surface so as to allow easy access and repair without removal of the port closures.

Another object is to provide port closure means which is constructed so as to connect a pressurized fluid source with the interior fluid jacket conduits of engine cylinder heads or similar structures for testing purposes.

Another object is to provide simplified universal clamping means adaptable to cylinder heads of various design for securing port closure members and sealing the ports.

Another object is to provide testing apparatus of the character described which allows the rapid testing of substantially heavier diesel engine cylinder heads and similar parts.

Other objects and advantages of our invention will be made apparent in the course of the following description of preferred forms of the invention.

BRIEF DESCRIPTION OF THE DRAWINGS

Referring to the accompanying drawings, which are for illustrative purposes only:

FIG. 3 is an enlarged fragmentary sectional view taken substantially on line 3—3 of FIG. 1 disclosing the construction of the head clamping assembly;

FIG. 4 is an enlarged fragmentary sectional view taken substantially on line 4—4 of FIG. 3 disclosing a longitudinal view of the clamping means by which the head is secured to the testing frame assembly and the port closure means of the testing apparatus.

FIG. 5 is an enlarged fragmentary sectional view of FIG. 4 taken substantially on line 5—5 showing a detailed sectional view of a port closure member;

FIG. 6 is an enlarged sectional view of FIG. 2 taken substantially along line 6—6 and discloses the construction of a port closure member adapted for supplying a pressurized fluid to an engine cylinder head fluid jacket;

FIG. 7 is an enlarged plan view of the mating surface of a port closure member disclosing the construction of the sealing means;

FIG. 8 is a detailed perspective view of a clamp bar used in clamping a cylinder head to the support frame;

FIG. 9 is an enlarged fragmentary sectional view disclosing the construction of the sealing means of the port closure member illustrated in FIG. 5;

FIG. 10 is an enlarged fragmentary sectional view of a port closure structure disclosing the axial positioning of the clamping plate as it bears on the domed surface of the port closure member; and FIG. 11 is an enlarged sectional view of the locking pivot structure of FIG. 1 taken along line 11—11.

DESCRIPTION OF THE PREFERRED EMBODIMENT

Figure 1:
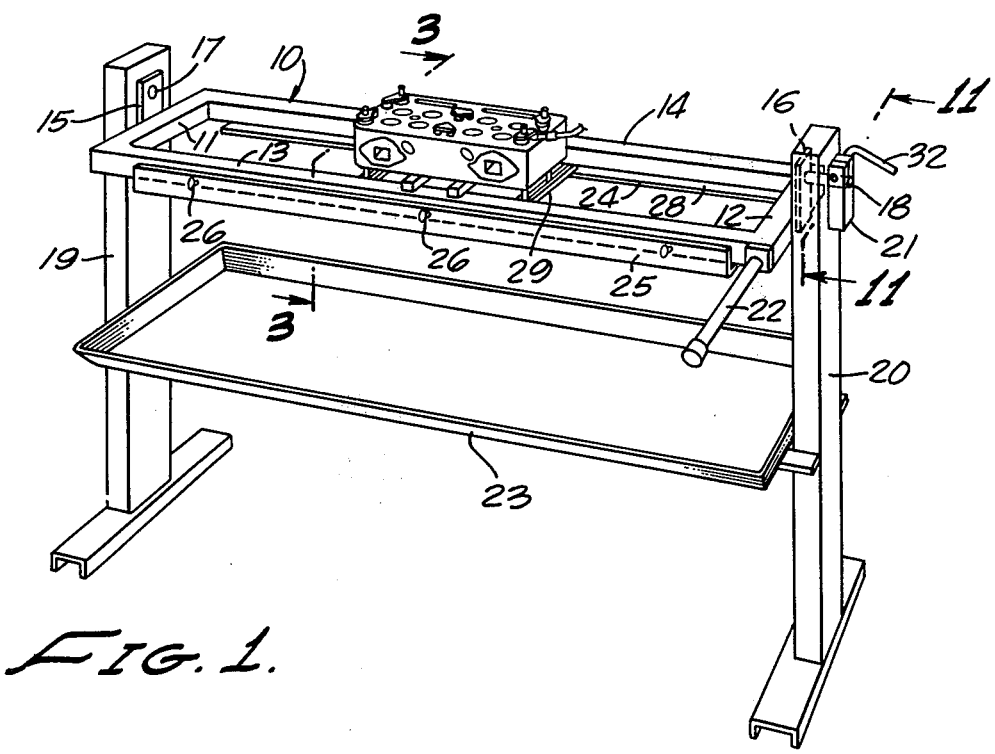
FIG. 1 is a perspective view of apparatus according to the present invention.

Referring more specifically to the drawings for illustrative purposes the testing apparatus of the present invention is disclosed in FIG. 1 as comprising generally a pivotally mounted, rigid, rectangular frame structure 10 upon which a cylinder head is secured, ready for testing procedures that will ascertain the presence of defects that cause leakage so that they may be repaired by conventional methods and procedures without removing the head from the testing apparatus.

More specifically the rectangular frame 10 includes rigid end rails 11 and 12 and side rails 13 and 14. The end rails 11 and 12 are connected to tabular members 15 and 16 which in turn are connected by pivot pins 17 and 18 to pedestal support means 19 and 20 such that the frame structure may be made to pivot about an axis located above and longitudinal of the length of the frame structure by means of a handle 22. The pivoting of the frame structure about an axis located above the plane of the frame facilitates manipulation and positioning of the part to be tested as the rotational axis closely coincides with the center of gravity of the part when it is mounted on the frame.

The frame structure once adjusted to a desired angle may be locked into position by locking means 21, as shown in FIG. 11, which frictionally engages the pivot pin 18 by tightening handle 32. The ability to lock the frame structure at a given angle enables more rapid installation of port closure members on the head and provides easier access when repairing cracks or leaks in the head.

Located below the frame structure 10 and attached to the pedestal support means is a pan assembly 23 where tools or other materials used in the testing procedures may be kept.

As shown in FIG. 1 and in more detail in FIG. 2 and FIG. 3 the rectangular frame structure 10 has angle support bars 24 and 25 located longitudinally of and in contact with the frame side rails 13 and 14 and secured to the side rails by means of thumb screws 26 such that two opposing channelways 27 and 28 are disposed longitudinal of and immediately below the frame side rails 13 and 14. The angle support bars 24 and 25, more clearly shown in FIG. 2, support and allow rapid lateral positioning of clamp bars, and FIG. 8 which are installed in the channelways 27 and 28. The clamp bars 29 are used to secure the engine part to be tested to the frame structure and are positioned crosswise of the frame side rails 13 and 14 in the channel ways 27 and 28 located between the angle support bars 24 and 25 and the frame side rails 13 and 14. The clamp bars may be positioned laterally along the length of the angle support bars so as to accommodate cylinder heads of various configurations.

Figure 2:
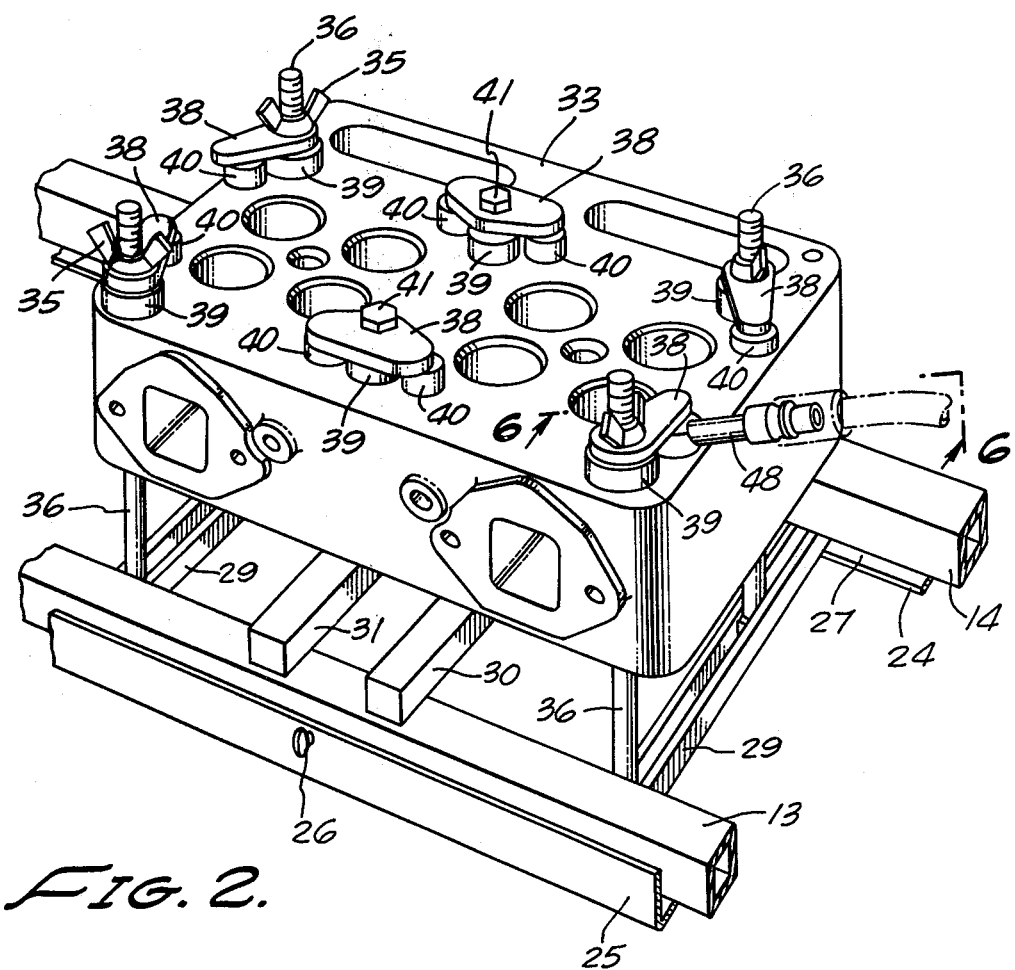
FIG. 2 is an enlarged view of a cylinder head mounted in position on the testing apparatus and ready for testing.

Rest bars 30 and 31 as shown in FIG. 2 and FIG. 3 are placed on top of and extending across the frame side rails so that an engine component such as a diesel engine cylinder head may be positioned on the rest bars with its gasket mating surface 33 face up. The rest bars 30 and 31 are placed in a position where they do not interfere with access to the stud bolt holes 34 to be used in securing the cylinder head to the frame structure or those used in clamping and sealing the engine ports 42.

As shown in FIGS. 2, 3 and 4 "T"-bolts 36 are brought up through the clamp bars 29 and through stud bolt holes 34 in the cylinder head. Wing nuts 35 may then be fastened to the "T"-bolts 36 thereby securing the cylinder head to the rest bars 30 and 31 and the frame side rails 13 and 14. The heads 38' of the "T"-bolts 36 are constructed with means to prevent rotation of the bolt when the "T"-bolts are brought up through the clamp bars 29. A portion of the "T"-bolt head 38' is engaged in the slot in the clamp bar 29 preventing rotation of the "T"-bolt while securing the head to the frame structure, thus enabling more rapid setup of the head on the testing apparatus.

As shown by FIGS. 2 and 3 the T-bolts 36 may also serve in some cylinder head configurations to hold clamp plates 38 in place, thereby applying pressure and sealing the port closure members 40 as well as securing the cylinder head to the frame structure.

In general the above described procedure of mounting a cylinder head on the frame structure applies to engine cylinder heads of any manufacture, however, in instances where longer heavier diesel heads are being tested it may be necessary to use three or more clamp bars or rest bars in securing the heads to the testing frame. Also given differing cylinder head configurations and stud bolt patterns, the size and length of the tie-down "T"-bolts used in clamping the head to the tester may vary.

Once the cylinder head is secured to the frame assembly its fluid circulating ports may be sealed so that the head can be tested by means of subjecting the water-jacket conduits to a pressurized fluid and then using a suitable soap solution or other solution on the exterior of the pressurized head to detect leaks or cracks which the may be repaired.

Diesel engines operate at significantly higher compression pressures then standard gasoline engines and cracks or leaks that would not be readily apparent at lower gasoline engine compression pressures become apparent at the higher pressures encountered in diesel engine operation.

Thuse one of the problems in testing diesel engine cylinder heads is sealing the fluid-circulating ports so that a fluid under sufficient pressure can be introduced into the fluid jacket conduits so as to detect small leaks or cracks present under the pressures encountered in diesel engine operation.

A major advantage of our invention, as disclosed herein, over existing art is the construction of the port sealing structures which provide for faster set up and sealing of the cylinder head to withstand higher test pressures while leaving the gasket surface of the head relatively unobstructed so as to permit repair of the defect without necessitating the removal of the test equipment.

Port closure members 40 as shown in FIGS. 2, 3 and 4 for sealing the fluid jacket ports on the gasket surface or face of the cylinder head are installed over the ports to be closed and are secured by means of clamps comprising a clamp plate 38, a clamp bolt bushing 39 and a stud bolt 41 or "T"-bolt 36 depending upon the configuration of the cylinder head being tested.

More specifically, as illustrated in FIGS. 5 and 7, the port closure members 40 which may be constructed of metal or other suitable material are of a design similar to that of a stopper or plug whereby the lower section of the closure member is of a diameter slightly smaller than the diameter of the port opening to be sealed, such that the neck of the plug closure member extends into the port opening 42, but does not serve as a means of sealing the port. This feature provides for rapid positioning and centering of the port closure members in the ports and prevents the closure members from sliding off the cylinder head face if the frame structure is set at an angle during installation.

The head portion of the port closure member 40 when installed on the cylinder head rests on the head's gasket face surface 33 and has in its flanged sealing surface an annular groove 45 wherein an O-ring gasket 46 of rubber or other suitable material may be placed so as to provide sealing means when the closure member has pressure applied thereon by the clamp plate 38. As shown in FIGS. 7 and 9 the annular groove 45 designed to receive the O-ring seal 46 is constructed such that it has a diameter greater than that of the port opening so that when the port closure member 40 is installed on the port 42 and pressure is applied to the closure member 40 sealing the port by compressing the O-ring 46, the O'ring seal is prevented from contacting the pressurized fluid in the fluid circulating jacket.

In order to promote an effective seal between the closure member 40 and the cylinder head gasket surface 33, the head surface 43 of the closure member 40 possesses a domed configuration as shown in FIGS. 5 and 10. When a clamp plate 38 is placed in contact with the domed head surface 43 of the closure member and pressure applied by securing the clamp plate 38 with either a stud bolt 41 or a "T"-bolt 36 as shown in FIG. 2 or 4, pressure is applied along the vertical axis of the closure member irrespective of the fact that the clamp plate 38 may be slightly inclined to the closure member, as shown in FIG. 10, due to unevenness of the cylinder head or unequal thicknesses of the clamp bolt bushings 39. This feature allows the closure members to evenly seat on the head surface, thereby eliminating any tendency to tilt and allow gaps through which the pressurized fluid in the head can escape.

As described earlier in certain cylinder head configurations, as best illustrated by FIG. 2, the ports to be sealed may be located adjacent to the stud bolt holes 34 containing the "T"-bolts 36 used to secure the head to the frame structure. In such instances the "T"-bolts 36 may be used to clamp the port closure members 40 thereby sealing the ports by placing a clamp bolt bushing 39 on the "T"-bolt 36 projecting through the face of the cylinder head 33; placing an appropriately shaped clamp plate 38 on the "T"-bolt such that the clamp plate 38 comes in contact with and bears on the closure member 40; placing a wing nut 35 on the "T"-bolt 38 and thereby securing the port closure member and sealing the port so that a pressurized fluid can be introduced into the fluid circulating cavities to test for cracks, leaks or other defects.

In order to supply a pressurized fluid to the fluid-circulating jacket conduits of the cylinder head one of the port closure members possesses a modified construction as shown in FIG. 6. The port closure member 40 as shown in FIG. 6 is constructed with an internal bore 47 which provides communication between the fluid jacket conduits 42 and a tubular member 48 affixed to one end of the bore. The tubular member may then be attached by quick-connect-disconnect means to a pressurized fluid supply conduit whereby pressurized fluid may be introduced into the cylinder head for the purpose of detecting leaks or cracks.

Thus, as illustrated in FIG. 2 a diesel head is mounted on the testing apparatus with ports closed and ready for testing using eight port closure members 40, six clamp plates 38, two stud bolts 41, four "T"-bolts 36 and eight clamp bolt bushings 39. In contrast to testing apparatus disclosed in the prior art on our invention the head is exposed and readily accessible for testing and/or repair with a minimal obstruction of the head surface by the port closure structures.

Various modifications may suggest themselves to those skilled in the art without departing from the spirit of our invention, and hence, we do not wish to be restricted to the specific form shown or uses mentioned, except to the extent indicated in the appended claims.

We claim:

1. Apparatus for the fluid pressure testing of engine cylinder heads and similar parts having a fluid circulating jacket containing communicating ports which open into a mating connecting surface comprising:
    (a) a frame structure possessing a pair of end rails connected to a pair of side rails so as to form a rigid rectangular framework;
    (b) means for supporting said frame structure;
    (c) means pivotally connecting said frame structure to said frame support means so that said frame structure is free to pivot about an axis longitudinal of said frame structure;

(d) means for locking said pivoting connecting means of said frame structure in one or more fixed positions to prevent pivoting of said frame structure;

(e) means for supporting the part to be tested on said frame structure with said part's mating surface exposed and substantially above the plane of said frame structure, said part supporting means extending across and immediately above said side rails;

(f) means for securing the part to be tested to said frame structure so that said part supporting means and said part are rigidily affixed to said frame structure;

(g) a plurality of port closure members for individually covering and sealing said ports when pressure is applied to the top surface of said closure member;

(h) means for independently clamping and mechanically applying pressure uniformly to said closure members, sealing said ports; and (i) means for introducing a pressurized fluid into the sealed fluid-jacket conduits for the purpose of detecting cracks or leaks in the part being tested.

2. The apparatus as defined in claim 1, wherein said pivoting connecting means comprises:

pivot pins positioned on an axis longitudinal of and above the plane of said frame structure and substantially close to the center of gravity of a part to be tested when mounted on said frame structure, and clamp means for frictionally engaging and locking said pivoting connecting means.

3. The apparatus as defined in claim 1 wherein said engine part securing means comprises:

(a) two angle support members positioned longitudinal of and secured to said frame side rails by connecting means so that two opposing channel ways are located below and along the length of said side rails;

(b) two or more clamp bar means, each of said clamp bars comprising two closely spaced, substantially parallel bars joined by connecting means at either end, said clamp bars extending across said frame side rails being supported and laterally adjustable in the channels created by said angle support members; and (c) connecting means extending upward through said clamp bars and continuing through holes in the part being tested, being secured to said part by threaded fasteners so that upon tightening said fasteners on the connecting means said clamp bar is mechanically drawn up against said frame side rails so as to clamp said part securely to said frame structure.

4. The apparatus as defined in claim 1 wherein said port closure comprises:

(a) a substantially circular plug having a domed top surface, a flanged mating surface for seating on the mating connecting surface of the part to be tested and a neck section of a diameter slightly less than the diameter of said port so that said neck extends into said port centering said plug on said port;

(b) gasket means positioned in an annular groove in said flanged mating surface, said annular groove possessing a diameter greater than the diameter of said port.

5. The apparatus of claim 4, in which said port closure member includes conduit means for communicating between the interior of said fluid circulating jacket of the part and a pressurized fluid source.

6. Apparatus for the fluid pressure testing of engine cylinder heads and similar parts possessing a fluid circulating jacket containing communicating ports which open to a mating connecting surface comprising:

(a) a frame structure possessing a pair of end rails connected to a pair of side rails to form a rigid, rectangular framework;

(b) angular support members secured by connecting means to the side rails of frame structure and extending longitudinal of said side rails so that a pair of opposing channel ways are located below and along the length of said side rails;

(c) means for supporting said frame structure;

(d) means pivotally connecting said frame structure to said frame support means so that said frame structure pivots on an axis longitudinal of and above the plane of the frame structure and substantially close to the center of gravity of a part to be tested when mounted on said frame structure;

(e) means for locking said pivoting connecting means of said frame structure in one or more fixed positions to prevent pivoting of said frame structure;

(f) means for supporting the part to be tested on said frame structure with said part's mating surface exposed so that said part support means extends across said side rails;

(g) two or more clamp bar means, each of said clamp bars comprising two closely spaced, substantially parallel bars joined by connecting means at either end, said clamp bars extending across said frame side rails being supported and laterally adjustable in the channels created by said angle support members;

(h) connecting means extending upwards between the closely spaced members of said clamp bars and continuing through holes in the part being tested, being secured to said part by wing-nuts so that upon tightening of the wing-nuts on the connecting means said clamp bar is mechanically drawn up against said frame side rails so as to clamp said part to said frame structure; and (i) a plurality of port closure structures each of said structures comprising a substantially circular plug possessing a domed top surface, an annular flanged mating surface for seating on the mating surface of the part to be tested, a neck section of a diameter slightly less than the diameter of said port so as to extend into said port for centering of said plug, gasket means positioned in an annular groove in said annular flanged mating surface, said groove possessing a diameter greater than the diameter of said port, clamping means for independently applying pressure on said port closure plug said means being secured to said part to be tested by connecting means so that by tightening said connecting means, said clamp means mechanically applies pressure along the axis of said closure plug sealing said port.

* * * * *